(12) United States Patent
Leinonen

(10) Patent No.: US 6,817,715 B2
(45) Date of Patent: Nov. 16, 2004

(54) METHOD AND A DEVICE FOR MEASURING READING ABILITY AND/OR VISUAL ACUITY

(76) Inventor: Markku Leinonen, Paltankatu 33, FIN-20360 Turku (FI)

(*) Notice: Subject to any disclaimer, the term of this patent is extended or adjusted under 35 U.S.C. 154(b) by 116 days.

(21) Appl. No.: 10/220,473

(22) PCT Filed: Mar. 15, 2001

(86) PCT No.: PCT/FI01/00255
§ 371 (c)(1),
(2), (4) Date: Aug. 30, 2002

(87) PCT Pub. No.: WO01/74228
PCT Pub. Date: Oct. 11, 2001

(65) Prior Publication Data
US 2003/0103192 A1 Jun. 5, 2003

(30) Foreign Application Priority Data
Mar. 24, 2000 (FI) .............................. 20000691

(51) Int. Cl.[7] .............................. A61B 3/02; A61B 3/00
(52) U.S. Cl. ...................... 351/222; 351/239; 351/246; 434/178; 434/179
(58) Field of Search ................................. 351/222, 239, 351/246; 434/156, 178, 179–180

(56) References Cited

U.S. PATENT DOCUMENTS

| | | | |
|---|---|---|---|
| 824,900 A | 7/1906 | Bates | |
| 1,657,601 A | 1/1928 | Armbruster | |
| 2,583,205 A | 1/1952 | Boisen | 33/161 |
| 4,415,243 A | 11/1983 | Gottlob et al. | 351/201 |
| 4,714,330 A | 12/1987 | Hennequin | 351/239 |
| 5,129,720 A | 7/1992 | Jovicevic | 351/243 |
| 5,220,362 A | 6/1993 | Blenkle | 351/235 |
| 5,861,941 A | 1/1999 | Liebers et al. | 351/245 |

Primary Examiner—Brian L. Casler
Assistant Examiner—John R. Sanders
(74) Attorney, Agent, or Firm—James C. Lydon

(57) ABSTRACT

A method for measuring reading ability in which the test subject reads passages at a predetermined distance from the eyes of the test subject, the text size of the passages varying in steps in the reading order, the measurer assessing the test subject's reading ability on the basis of what the measurer hears. Each text passage contains at least one numeral word, indicating the visual acuity required by the passage. An auxiliary device for positioning the test subject's eyes at a desired distance from the object being viewed includes a plurality of parts of different lengths, linkable to one another in succession, from which parts the length corresponding to each desired distance is obtained by selecting and, when necessary, by linking the parts together.

10 Claims, 4 Drawing Sheets

FIG. 4

Figure 1:
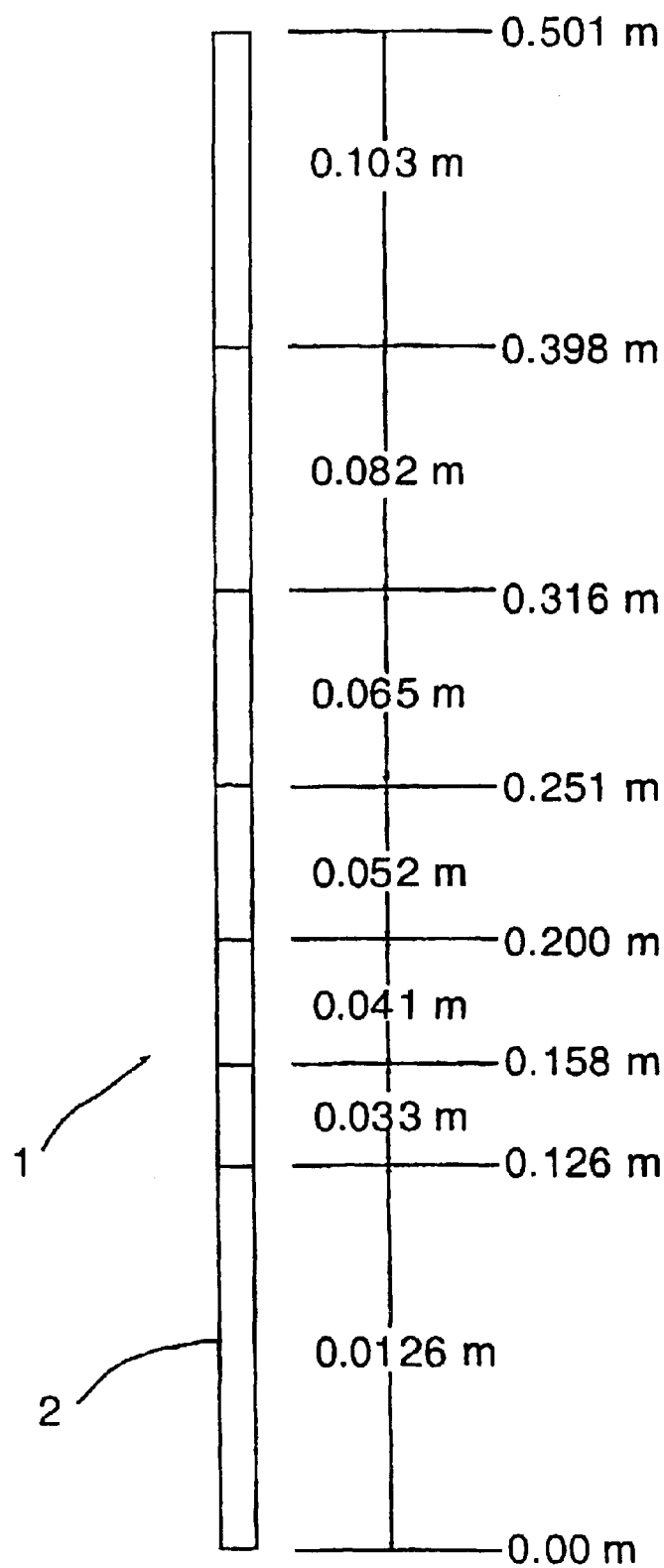

```
eight which development account road rapidly now stalemate
two their being ministerial zero plentiful over be team
subconscious two team if internet percentage are five filled
personal three decrease were two

METHOD AND A DEVICE FOR MEASURING READING ABILITY AND/OR VISUAL ACUITY

This application is a U.S. National Stage of International application PCT/FI01/00255, filed Mar. 15, 2001 and published on Oct. 11, 2001 in the English Language.

The present invention relates to a method for measuring reading ability and specifically to a method wherein the test subject reads text passages of the same length at a specific distance from the test subject's eyes, the text size of the passages varying preferably stepwise in the order in which the text passages are read and the measurer assessing on the basis of what he hears the reading ability of the test subject.

This invention additionally relates to an auxiliary device intended for use not only in the above-mentioned measuring of reading ability, but also generally in measuring visual acuity, for positioning, and preferably also for maintaining, the test subject's eyes at the desired distance from the object being viewed, such as a text passage or a display screen, such as a so-called eye-test chart or E-chart.

In known methods for measuring reading ability, the test subject reads aloud sentences on paper or a display screen at a predetermined distance, the sentences making sense by their vocabulary, grammatical structure and train of thought.

When known methods for measuring reading ability are applied repeatedly to one and the same person, for example, when testing the effect of eyeglasses of different strengths on the reading ability, the measuring result is distorted, since the test subject may remember the contents of the sentences from a preceding measuring round and may, even the first time, to a varying degree guess correctly some of the words in the sentences.

When reading ability is being measured with a very small letter size, checking the correctness of the reading may be difficult, since it may be difficult for the measurer to see well a text in a very small letter size, and thus, following the test subject's reading may prove to be difficult. It is also difficult to observe when the test subject shifts to the subsequent text passage, written in a different letter size.

In known methods for measuring reading ability, the test subject reads the text aloud for the checking of the correctness of the reading. In this case the maximum speed of reading cannot be detected, since reading aloud slows down the reading.

In known methods for measuring reading ability, as well as visual acuity in general, it is important to know and maintain the distance of the test subject's eyes from the text passage or the so-called E-chart in general used for measuring visual acuity.

In known methods, visual acuity is calculated by dividing the freely selected viewing distance used by a numeric value indicated in meters, the value expressing the size of the letter or optotype viewed in so-called M-units. The size of the letter or optotype is 1 M-unit if the size of its detail at a distance of 1 meter is 1 minute of arc. This, however, requires a calculation, and another drawback is that, when the viewing distance is freely selected, it seldom corresponds to the established numeric values of visual acuity, which constitute a series decreasing from the normal visual acuity of 1.0 in steps having the magnitude of 0.1 log unit.

The object of the present invention is to eliminate the disadvantages mentioned above and to provide a method of the type cited in the preamble for measuring reading ability, wherein memorizing or guessing by the test subject will not distort the measuring results, reading aloud will not slow down the reading, and a text in a very small letter size will not make assessment by the measurer more difficult.

It is a further object of the invention to provide an auxiliary device for setting the viewing distance and preferably for maintaining it at such a distance from the object being viewed, such as a text passage, a letter or an optotype, that at all of the viewing distances that can be selected the calculated numeric values of visual acuity will comply with the above-mentioned established logarithmic numeric series. With the auxiliary device of the invention the viewing distance may additionally be altered rapidly so that at each level of visual acuity the test subject will be able to see a letter size precisely one step smaller if the viewing distance decreases by one step, and respectively a letter size one step larger if the viewing distance increases by one step.

The main characteristics of the invention are given in the enclosed claims.

In the method according to the invention for measuring reading ability there is thus in each text passage at least one written numeral word, which indicates the visual acuity required by the said text passage at the nominal distance of the eye-test chart. Thus a text a small letter size will not hamper the assessing of visual acuity by the measurer.

In the text passages there are, however, preferably many numeral words, each text passage starting with the same numeral word, which is not included in the numbers indicating visual acuity. Thus the measurer is able easily and reliably to note the transfer of the test subject from one text passage to another and to measure the reading time required of the test subject by each text passage.

The measurer is able easily to conclude the visual acuity required by each text passage, since the numeral word or words indicating it follow immediately the numeral word at the beginning of the passage, indicating the changing of the text passage. Any subsequent numeral words, on the other hand, may be random, but it is preferable to select them in order from a numeric series commonly used for indicating visual acuity. Since a person skilled in the art easily memorizes this numeric series, it is easy for him to observe the flawlessness of the reading by the test subject even if the numeric series were not visible to him anywhere.

The letter size, in M units, of successive text passages preferably varies in steps so that the numeric values of the letter size, when necessary as multiples of ten, are the same as in the numeric series used for indicating visual acuity and which is a numeric series decreasing from the normal visual acuity 1.0 in steps of the magnitude of 0.1 log unit.

The test subject is preferably requested to read aloud only the numeral words in the text passages, in which case reading aloud will slow down the reading speed as little as possible, but the test subject will, however, have to read the entire text in order to see where there are numeral words.

The words in the text passages are preferably random words picked out from a large number of normal sentences which make sense, and so the words cannot be guessed and their order cannot be easily remembered, since they do not come in a logical order.

The auxiliary device intended for use in the measuring of reading ability or visual acuity, for positioning the eyes of the test subject and, when necessary, for maintaining them at a specific distance from the object to be viewed, comprises according to the invention a series of parts of different lengths, to be linked to one another in succession, and by selecting from them and, when necessary, linking them together, a length corresponding to each desired distance is obtained and the distances thus need not be measured separately. The desired distances are predetermined in such a manner that at each level of visual acuity the test subject is able to see a letter size precisely one step smaller if the viewing distance decreases by one step, and respectively a letter size one step larger if the viewing distance increases by one step. The calculated numeric values of visual acuity at all the selectable viewing distances additionally follow the above-mentioned established logarithmic numeric series.

The lengths, in meters, of the separate parts linked successively therefore follow the established numeric values of visual acuity, i.e. they form a series decreasing from the normal value (1.0) at intervals of 0.1 log unit, when necessary, in multiples of ten.

The parts of the auxiliary device set are preferably elongated pegs having at one end an axial recess and at the opposite end a likewise axial projection the outer dimensions of which correspond to the inner dimensions of the recess, so that the pegs can conveniently be linked in succession by pushing the projection of one peg into the recess of the successive peg.

The cohesion of the device assembled from the pegs is ensured by means of a stretchable fastening member, such as a rubber band or an elastic band, tightened between its ends. The pegs are preferably hollow, in which case the cohesion of the auxiliary device assembled from pegs, and the correct order of the pegs, can be ensured by means of the said fastening member tightened inside the pegs.

In the measuring of reading ability and visual acuity, usually each eye is tested separately, and for this purpose the auxiliary device is preferably provided with a plate fitted between two parts transversally and projecting from the auxiliary device, i.e. with an eye cover, which can by suitable rotation be set selectively in front of the test subject's left or right eye, between the eye and the object being viewed, and which prevents the test subject from making the viewing distance shorter than intended.

The method according to the invention is described below in greater detail with the help of an example:

EXAMPLE

On the display screen or chart to be viewed there are preferably at the same time several passages of text, one below the other, the letter size changing gradually from one text passage to the next. The letter size, in M-units, in successive text passages varies preferably in steps so that the numeric values of the letter size, when necessary, in multiples of ten, are the same as in the numeric series used for expressing visual acuity and which is a numeric series decreasing from the normal visual acuity 1.0 in steps of 0.1 log unit; 1.0; 0.79; 0.63; 0.50; 0.40; 0.32; 0.25; 0.20; 0.16; 0.13; 0.10. Numeral words are scattered among the random words of the text passages. One text passage in a specific text size reads as follows:

"eight which development account road rapidly now stalemate two their being ministerial zero plentiful over be team subconscious two team if internet percentage are five filled personal three decrease were two treasurer four supported immobile zero."

The display screen or chart is at a constant distance from the test subject's eyes, and the test subject is asked to read the text passages in order, but to read aloud only the numeral words. In this case the numeral words are, in the order of appearance: eight, two, zero, two, five, three, two, four, zero. The first numeral word, "eight," which is not included in the values commonly used in visual acuity, indicates that the test subject has started the reading of a new text passage; from this the measurer can measure the time used for the reading of the text passage and can note down the next numeral words following, "two" and "zero," which indicate the number 0.20, which indicates the reading ability required by the text passage. Number 2.0 is out of the question, since the visual acuity of the human eye usually does not reach such a value. The other numeral words are not necessarily significant in terms of the measuring. In this example, the subsequent numeral word pairs "two" and "five," "three" and "two," and "four" and "zero," are numeral words picked out of the above-mentioned numeric series, in this case in the reverse order, in order to facilitate the flawlessness of the test subject's reading.

Figure 2:
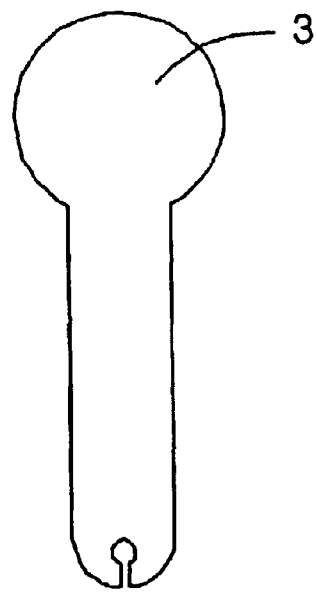
Figure 3:
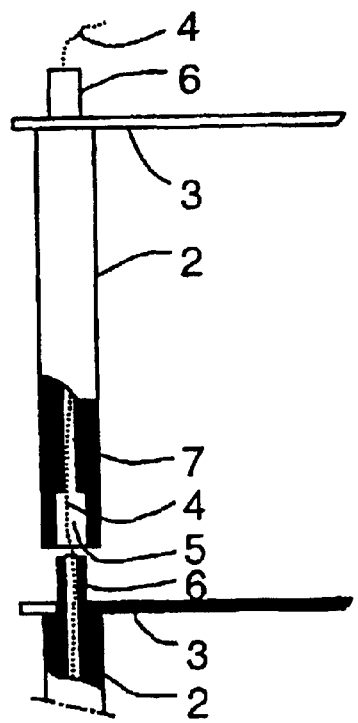
Figure 5:
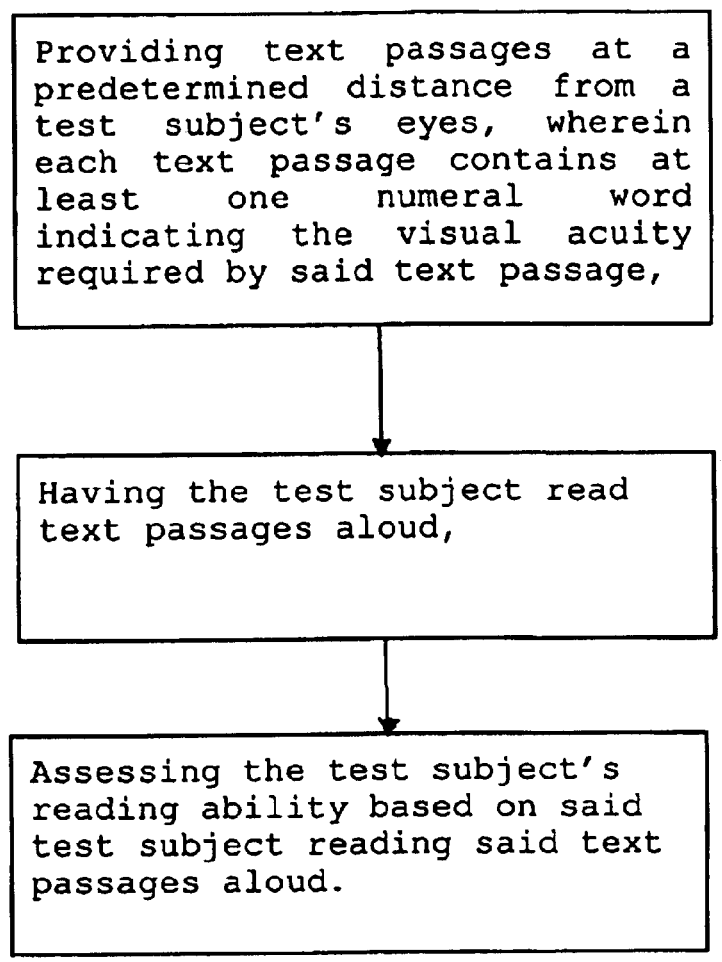

The auxiliary device according to the invention is described below in greater detail with the help of the accompanying drawing, wherein FIG. 1 depicts an auxiliary device assembled from pegs of different lengths, FIG. 3 depicts, partly in section, a peg used in the auxiliary device according to the invention, and FIG. 2 depicts, from the viewing direction, the eye cover intended for use in the auxiliary device according to the invention. FIG. 4 illustrates a text passage suitable for use in the invention, while FIG. 5 depicts a flow chart describing the method of the invention.

As is seen in FIG. 1, the auxiliary device, which is generally designated by reference number 1, is assembled from pegs 2 of different lengths, and the cohesion of the auxiliary device assembled from pegs 2 is ensured by means of an elastic band 4 tightened between its ends inside the hollow pegs 2. The length of each peg 2, in meters, is indicated in FIG. 1, as is also the length of the pegs in total.

It can be seen in the table below that the total length, in meters, of the successively linked parts of the auxiliary device follows precisely, and the lengths of the separate parts approximately, the established numeric values of visual acuity, i.e. they form a series decreasing from the normal value (1.0) at intervals of 0.1 log unit, when necessary, in multiples of ten.

| Numeric series | Peg length (m) | Auxiliary device length (m) | Difference (m) | Difference (%) |
| --- | --- | --- | --- | --- |
| 1.000 | | | | |
| 0.790 | | | | |
| 0.600 | | | | |
| 0.501 | 0.103 | 0.501 | 0.000 | 0.0 |
| 0.398 | 0.082 | 0.398 | 0.000 | 0.0 |
| 0.316 | 0.065 | 0.316 | 0.000 | 0.0 |
| 0.251 | 0.052 | 0.251 | 0.000 | 0.0 |
| 0.200 | 0.041 | 0.200 | 0.000 | 0.0 |
| 0.158 | 0.033 | 0.158 | 0.000 | 0.0 |
| 0.126 | 0.126 | 0.126 | 0.000 | 0.0 |
| 0.100 | | 0.103 | 0.003 | 3.1 |
| 0.0794 | | 0.082 | 0.002 | 3.1 |
| 0.0631 | | 0.065 | 0.002 | 3.1 |
| 0.0501 | | 0.052 | 0.002 | 3.1 |
| 0.0398 | | 0.041 | 0.001 | 3.1 |
| 0.0316 | | 0.033 | 0.001 | 3.1 |

Numeric series = at intervals of 0.1 log unit (starting at 1.0) $L_{(a+1)} = L_a * 10^{-0.1}$ Since the letter size in the successive text passages follows the same numeric series, there are obtained for the values of visual acuity, calculated for the different distances (visual acuity=viewing distance/smallest letter size seen) numbers which also follow the same numeric series, as is shown by the following table:

| Letter size (M) | Viewing distance (m) | | | | | | | | | | |
|---|---|---|---|---|---|---|---|---|---|---|---|
| | 0.050 | 0.063 | 0.079 | 0.10 | 0.13 | 0.16 | 0.20 | 0.25 | 0.32 | 0.40 | 0.50 |
| 0.20 | 0.25 | 0.31 | 0.40 | 0.50 | 0.63 | 0.79 | 1.0 | 1.3 | 1.6 | 2.0 | |
| 0.25 | 0.20 | 0.25 | 0.32 | 0.40 | 0.50 | 0.63 | 0.79 | 1.0 | 1.3 | 1.6 | 2.0 |
| 0.32 | 0.16 | 0.20 | 0.25 | 0.32 | 0.40 | 0.50 | 0.63 | 0.79 | 1.0 | 1.3 | 1.6 |
| 0.40 | 0.13 | 0.16 | 0.20 | 0.25 | 0.32 | 0.40 | 0.50 | 0.63 | 0.79 | 1.0 | 1.3 |
| 0.50 | 0.10 | 0.13 | 0.16 | 0.20 | 0.25 | 0.32 | 0.40 | 0.50 | 0.63 | 0.79 | 1.0 |
| 0.63 | 0.079 | 0.10 | 0.13 | 0.16 | 0.20 | 0.25 | 0.32 | 0.40 | 0.50 | 0.63 | 0.79 |
| 0.79 | 0.063 | 0.079 | 0.10 | 0.13 | 0.16 | 0.20 | 0.25 | 0.32 | 0.40 | 0.50 | 0.63 |
| 1.0 | 0.050 | 0.063 | 0.079 | 0.10 | 0.13 | 0.16 | 0.20 | 0.25 | 0.32 | 0.40 | 0.50 |
| 1.3 | 0.040 | 0.050 | 0.063 | 0.079 | 0.10 | 0.13 | 0.16 | 0.20 | 0.25 | 0.32 | 0.40 |
| 1.6 | 0.032 | 0.040 | 0.050 | 0.063 | 0.079 | 0.10 | 0.13 | 0.16 | 0.20 | 0.25 | 0.32 |
| 2.0 | 0.025 | 0.032 | 0.040 | 0.050 | 0.063 | 0.079 | 0.10 | 0.13 | 0.16 | 0.20 | 0.25 |
| 2.5 | 0.020 | 0.025 | 0.032 | 0.040 | 0.050 | 0.063 | 0.079 | 0.10 | 0.13 | 0.16 | 0.20 |
| 3.2 | 0.016 | 0.020 | 0.025 | 0.032 | 0.040 | 0.050 | 0.063 | 0.079 | 0.10 | 0.13 | 0.16 |
| 4.0 | 0.013 | 0.016 | 0.020 | 0.025 | 0.032 | 0.040 | 0.050 | 0.063 | 0.079 | 0.10 | 0.13 |
| 5.0 | 0.010 | 0.013 | 0.016 | 0.020 | 0.025 | 0.032 | 0.040 | 0.050 | 0.063 | 0.079 | 0.10 |
| 6.3 | 0.0079 | 0.010 | 0.013 | 0.016 | 0.020 | 0.025 | 0.032 | 0.040 | 0.050 | 0.063 | 0.079 |
| 7.9 | 0.0063 | 0.0079 | 0.010 | 0.013 | 0.016 | 0.020 | 0.025 | 0.032 | 0.040 | 0.050 | 0.063 |

It can be seen in FIG. 3, that at one end of each peg 2 there is a axial recess 5 and at its opposite end an axial projection 6 of the same size and shape, in which case the pegs 2 can be linked to one another in succession by fitting the projection 6 of one peg into the recess of the subsequent peg 2, as is shown in greater detail in FIG. 1. The elastic band 4 is located in an axial hole 7 inside the peg 2.

FIG. 2 shows an eye cover 3, which can be fastened to the auxiliary device 1, shown in FIG. 1, between two pegs 2 at a suitable distance from the beginning of the device (0.00). By a suitable rotation of the eye cover 3 or the entire auxiliary device 1 the cover 3 can be placed in front of one eye of the test subject for the duration of the measuring.

The invention can be varied within wide limits within the scope of the enclosed claims, as is clear for a person skilled in the art.

Thus, for example, each text passage need not begin with the same numeral word not included in the numbers indicating visual acuity; alternatively, the text passages may end in the said numeral word, in which case each text passage begins with a numeral word or words indicating the visual acuity required by the said text passage.

What is claimed is:

1. A method for measuring reading ability, comprising providing text passages at a predetermined distance from a test subject's eyes, assessing the test subject's reading ability based on said test subject reading said text passages aloud, wherein each text passage contains at least one numeral word indicating the visual acuity required by said text passage.

2. The method of claim 1, wherein the text passages contain a plurality of numeral words and each text passage begins with the same numeral word, to indicate that the test subject has shifted from one text passage to another.

3. The method of claim 2, wherein of the numeral words in the text passage only the numeral word or words immediately subsequent to the numeral word beginning the text passage indicate the visual acuity required by said text passage, any other numeral words being random.

4. The method of claim 2, further comprising providing a numeric series of numbers which is used to indicate visual acuity of a test subject together with said text passages, with the proviso that the numeral word in a text passage is not a number of said numeric series.

5. The method of claim 3, wherein of the numeral words in the text passage only the numeral word or words immediately subsequent to the numeral word beginning the text passage indicate the visual acuity required by said text passage, any other numeral words being picked out in order from a numeric series which is used to indicate visual acuity.

6. The method of claim 1, wherein the test subject reads aloud only the numeral words in the text passages.

7. The method of claim 1, wherein all words in the text passages are in a random order.

8. The method of claim 1, wherein the text size varies so that the letter size of successive text passages in M-units is the same as in a numeric series which is used for indicating visual acuity and which is a numeric series decreasing from the normal 1.0 visual acuity in steps of 0.1 log unit.

9. The method of claim 8, wherein the text size varies in steps so that the letter size of successive text passages in M-units is the same as in a numeric series which is used to indicate visual acuity and which is a numeric series decreasing from the normal 1.0 visual acuity in steps of 0.1 log unit.

10. The method of claim 1, wherein the text size of the passages vary in steps in the order in which the text passages are to be read aloud by the test subject.

* * * * *